United States Patent [19]

Davison et al.

[11] 3,946,002

[45] Mar. 23, 1976

[54] PROCESS FOR PREPARING CEPHALOSPORINS

[75] Inventors: Michael Davison, St. Helens; David Binfield Frankham, Helsby, Near Warrington; Thomas William Matches Spence, Warrington, all of England

[73] Assignee: Lilly Industries Limited, London, England

[22] Filed: July 11, 1974

[21] Appl. No.: 487,489

[52] U.S. Cl.............................. 260/243 C; 424/246
[51] Int. Cl.².......................................... C07C 501/06
[58] Field of Search ................................. 260/243 C

*Primary Examiner*—Richard J. Gallagher
*Assistant Examiner*—Jose Tovar
*Attorney, Agent, or Firm*—William C. Martens, Jr.; Everet F. Smith

[57] ABSTRACT

An improved process for preparing antibacterially active 7-α-aminoacetamido cephalosporin-4-carboxylic acids in which a 7-aminocephalosporin-4-carboxylic acid ester is reacted with an activated form of an α-aminoacetic acid, the amino group of which is protected by a β-dicarbonyl group, this amino group being removed after the acylation in the presence of a sufficient amount of a hydrazine derivative to prevent re-reaction of the β-dicarbonyl protecting agent with the cephalosporin.

5 Claims, No Drawings

PROCESS FOR PREPARING CEPHALOSPORINS

This invention relates to an improved process for preparing cephalosporin compounds and more particularly the invention provides an improved method for preparing cephalosporins having an α-aminoacetamido substituent in the 7-position of the cephalosporin nucleus.

Many cephalosporin antibiotics having an α-aminoacetamido substituent are known, see for example the specifications of United Kingdom Patent Nos. 985747, 1174335, 1265315, 1276314, 1283811, 1284227 and 1288282. The known compounds disclosed in these and many other patent specifications may be encompassed by the general formula:

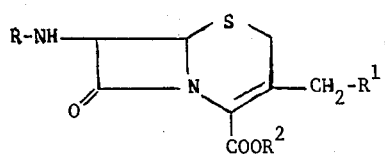
I where $R^1$ is hydrogen, hydroxy, acyloxy, or a thio substituent such as a heterocyclic-thio group; $R^2$ is hydrogen or a carboxylic acid protecting group; and R is the group

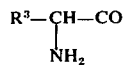

in which $R^3$ is a partially or fully unsaturated cyclic hydrocarbyl or heterocyclic group. The foregoing compounds can be prepared by reaction of the corresponding compound of formula I in which R is hydrogen and $R^2$ is a carboxylic acid protecting group with an activated form of the acid

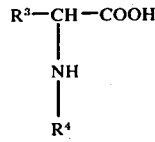

wherein $R^3$ is as defined above and $R^4$ is an amine protecting group, and thereafter removing the amine protecting group and if desired de-esterifying the resultant product to produce a compound of formula I in which $R^2$ is hydrogen. One suitable amine protecting group $R^4$ is the enamine formed by reaction with an appropriate β-dicarbonyl compound but the usefulness of this protecting group may on occasions be impaired by problems associated with the isolation of the desired product following cleavage of the enamine. Thus, due to the reactivity of the β-dicarbonyl compound regenerated by the cleavage reaction, it can re-react with the α-amino acetamido compound during subsequent purification and isolation steps causing loss of yield. This problem may be overcome by carrying out the enamine cleavage in such a manner that the free amino cephalosporin ester of formula I is precipitated from the reaction solvent, leaving the regenerated β-dicarbonyl compound in the mother liquors, and is then de-esterified, purified and isolated. Whilst the latter process removes the initial problem mentioned above, it does not cure the loss of yield since the introduction of the additional step of isolation of the free amino ester of formula I itself causes an equal if not greater loss of yield.

It is therefore an object of the present invention to provide an improved method for preparing 7-α-aminoacetamido cephalosporin compounds in which the α-amino substituent has been protected by enamine formation during the acylation reaction.

According to the broadest aspect of the present invention therefore, there is provided a process for preparing a 7-α-aminoacetamido cephalosporin-4-carboxylic acid which comprises:

a. reacting a 7-aminocephalosporin-4-carboxylic acid ester with an activated form of an α-aminoacetic acid, the amino group of which is protected by reaction with a β-dicarbonyl compound to form an enamine;

b. removing the amino protecting group from the resultant 7-α-aminoacetamido cephalosporin compound;

c. adding to the reaction mixture an amount of hydrazine or a derivative thereof sufficient to prevent re-reaction of the β-dicarbonyl compound with the 7-α-aminoacetamido cephalosporin compound produced in step (b); and d. if necessary, de-esterifying the resultant cephalosporin ester to produce the desired 7-α-aminoacetamido cephalosporin-4-carboxylic acid.

In step (a), the acylation is preferably carried out in a dipolar aprotic solvent such as dimethylformamide or acetonitrile. The acylation is normally carried out at temperatures around 0°C. or below, most advantageously in the range of −15°C. to −50°C.

The preferred 7-aminocephalosporin-4-carboxylic acid esters which may be acylated in accordance with the present invention are those of the formula:

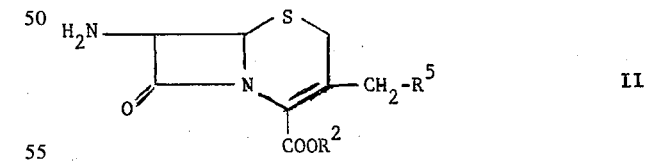
II and salts thereof, such as the hydrochloride and tosylate salts, wherein $R^2$ is as defined above and $R^5$ is hydrogen, acetoxy or a heterocyclic thio group, especially a thiadiazolylthio or tetrazolylthio group.

$R^2$ may be any of those groups commonly employed to protect the carboxylic acid function of the cephalosporin molecule. Illustrative of such groups are the benzyl, p-nitrobenzyl, p-methoxybenzyl, 3,5-dimethoxybenzyl, diphenylmethyl, 2,2,2-trichloroethyl, t- butyl, phenacyl, benzyloxymethyl and tetrahydropyranyl groups. Most advantageously, the compound of formula II is p-nitrobenzyl 7-aminodesacetoxycephalosporanate.

The protected α-aminoacetic acid used in step (a) is preferably one having the formula:

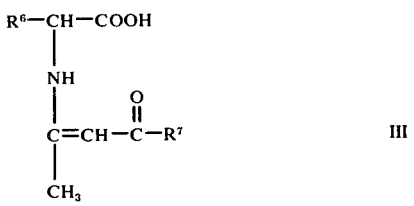

where $R^7$ is $C_{1-4}$ alkyl or $C_{1-4}$ alkoxy, preferably methyl, ethyl, methoxy or ethoxy and $R^6$ is a thienyl group, or a phenyl or cyclohexa-1,4-dienyl group optionally substituted by $C_{1-4}$ alkyl, $C_{1-4}$ alkoxy, halogen, hydroxy, amino, substituted amino, nitro or trifluoromethyl. The compounds of formula III are readily prepared by reaction of an acid of formula

or a salt thereof with a β-dicarbonyl compound of the formula $CH_3-CO-CH_2-CO-R^7$. Since the α-carbon atom of the acid of formula III is an asymmetric carbon, the acid can exist in two optically active isomeric forms, the D- and L-forms, as well as in the form of a racemic mixture. As will be appreciated, the configuration of the α-carbon of the acid of formula III is retained unchanged during the acylation reaction, and since the D-form of the end product cephalosporin is preferred, it is also preferred to use an acid of formula III which is in the D-form. Most advantageously, a D-acid of formula III, in which $R^6$ is unsubstituted phenyl, cyclohexa-1,4-dienyl or thienyl and $R^7$ is methoxy, is used.

As stated above, an activated form of the acid of formula III is used as the acylating agent in step (a). This activated form may be the acid chloride or anhydride but, preferably, is a mixed anhydride, for example one formed by reaction of a $C_{1-4}$ alkyl chloroformate, especially methyl chloroformate, with a salt of the particular acid.

In step (b) above, the amino protecting group is removed in a manner well known in the art, for example by acid hydrolysis using dilute acetic acid or hydrochloric acid. Following the hydrolysis, the free 7-α-aminoacetamido cephalosporin is obtained together with the regenerated β-dicarbonyl compound originally used to protect the α-aminoacetic acid acylating agent. At this stage, step (c), sufficient hydrazine or a derivative thereof such as hydrazine hydrate or preferably semi-carbazide or its hydrochloride is added to the reaction mixture to prevent re-reaction of the β-dicarbonyl compound with the α-amino group on the 7-acetamido cephalosporin. The hydrazine will normally be used in equimolar proportions with respect to the β-dicarbonyl compound but, if desired, an excess of the hydrazine may be used.

Following this step, if necessary, the resultant cephalosporin ester is de-esterified in the usual manner, for example by treatment with aqueous acetic acid and zinc dust, treatment with anhydrous trifluoroacetic acid, treatment with zinc and aqueous mineral acid such as hydrochloric acid, or by any other convenient mild hydrolysis or hydrogenolysis reaction, depending on the ester group to be removed. It will therefore be seen that, in many cases, the acid hydrolysis or hydrogenolysis used to cleave the enamine protecting group in step (b) will also accomplish the desired de-esterification and it is a preferred feature of the present invention that the ester and enamine groups used to protect the reactants of formulae II and III respectively should be so chosen as to permit such simultaneous removal. For example, if $R^2$ is p-nitrobenzyl and $R^7$ is methoxy, the use of zinc and hydrochloric acid in step (b) will simultaneously deblock the amino and carboxy functions to yield directly the desired 7-α-aminoacetamido cephalosporin-4-carboxylic acid which, following the addition of the hydrazine compound to the reaction mixture, may be purified and isolated in conventional manner.

A preferred use of the process of this invention is in the preparation of the cephalosporin antibiotic known as cephalexin, i.e. the compound of formula:

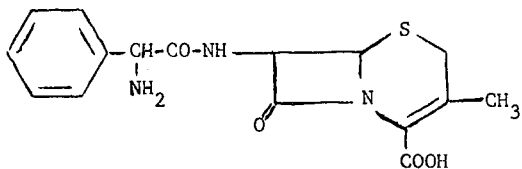

In preparing cephalexin by the present process, the p-nitrobenzyl ester of 7-aminodesacetoxycephalosporanic acid is reacted with a mixed anhydride of N-(2-methoxycarbonyl-1-methylvinyl)-D-α-phenylglycine in dimethylformamide, the resultant p-nitrobenzyl ester of 7-[N-(2-methoxycarbonyl-1-methylvinyl)-D-α-aminophenylacetamido]desacetoxycephalosporanic acid is reduced in an acidic medium to remove the amino and carboxy protecting groups, a hydrazine compound is added in sufficient amount to prevent re-reaction of the methylacetoacetate and cephalexin so produced, and the latter is then isolated in conventional manner to yield cephalexin of a high degree of purity. In particular, the resultant cephalexin is substantially free of the aromatic amine impurity which may be present in cephalexin produced by prior art processes involving the enamine protected phenylglycine acylation of the p-nitrobenzyl ester of 7-aminodesacetoxycephalosporanic acid. Although such prior art processes may produce cephalexin in high yield, the presence of the aforementioned aromatic amine impurity renders the cephalexin unusable without extensive additional purification steps which result in rapid overall loss of yield and substantial additional cost.

Whilst the foregoing description alone will teach those skilled in the art how to carry out the process of the present invention, the following Examples are given to illustrate the practical details involved in operating the improved process.

EXAMPLE 1

To a 1 liter flask containing dimethylformamide at 0°C., was added 24.8 g. sodium N-(2-methoxycarbonyl-1-methylvinyl)-D-α-phenylglycine (prepared from sodium D-α-phenylglycine and methyl acetoacetate). The mixture was cooled to −40°C. and methyl chloroformate (7.5 ml.) and dimethylbenzylamine (0.26 ml.) added. After stirring for 25 minutes, p-nitrobenzyl 7-aminodesacetoxycephalosporanate (32.8 g.) in the form of its hydrochloride salt was added, followed by triethylamine (12.1 ml.) and dimethylformamide (140 ml.) over a period of 20 minutes. The reaction mixture was stirred for 2 hours at −25° to −35°C., then warmed to 0°C. and water (32 ml.) added. To the resultant solution, hydrochloric acid (54 ml.) was added followed by zinc (21.8 g.) in portions over a period of 5 minutes, the temperature being maintained at 5 to 10°C. Further hydrochloric acid (35 ml.) was added and the solution stirred at 15° to 20°C. for 7 hours.

The pH was adjusted to 3.3 with triethylamine and semicarbazide hydrochloride (9.5 g.) added. The mixture was brought back to pH 3 with further triethylamine, then stirred for 30 minutes at pH 3. The resultant mixture was adjusted slowly over 4 hours to pH 6.8 by addition of triethylamine, seeding being carried out when pH 4.5 was reached. The precipitated cephalexin was filtered off, washed with dimethylformamide (200 ml.) and the cephalexin recovered, yield 75 percent.

EXAMPLE 2

The foregoing process was repeated except that the step of addition of semicarbazide hydrochloride was omitted. The yield of cephalexin fell to 48–52 percent, thus showing the value of the process of the present invention.

EXAMPLE 3

The process of Example 1 was repeated except that hydrazine hydrate (4.26 g.) was added instead of the semicarbazide hydrochloride. After the addition, the pH rose to 4.5 to 5.0, the reaction mixture was seeded and stirred for 30 minutes. The pH was then raised slowly to 6.8 as described in Example 1, the precipitated cephalexin filtered off, washed with dimethylformamide and recovered, yield 70–75 percent.

EXAMPLE 4

The process of Example 1 is repeated except that the sodium N-(2-methoxycarbonyl-1-methylvinyl)-D-α-phenylglycine is replaced by sodium N-(2-methoxycarbonyl-1-methylvinyl)-D-α-cyclohex-1,4-dienylglycine. An improved yield of cephradine is obtained as compared with that obtainable when the process is carried out in the absence of semicarbazide.

We claim:

1. In a process for preparing a 7-α-aminoacetamido cephalosporin in which (a) a 7-aminocephalosporin-4-carboxylic acid ester is reacted with an activated form of an α-aminoacetic acid, the amino group of which is protected by reaction with a β-dicarbonyl compound of the formula

in which $R^7$ is $C_1$–$C_4$ alkyl or $C_1$–$C_4$ alkoxy, to form an enamine; and (b) the amino protecting group is removed from the resulting protected 7-α-aminoacetamido cephalosporin compound; the step which comprises adding to the reaction mixture from step (b) an amount of a hydrazine or a semicarbazide sufficient to prevent re-reaction of the β-dicarbonyl compound with the produced 7-α-aminoacetamido cephalosporin.

2. Process according to claim 1, wherein the 7-aminocephalosporin-4-carboxylic acid ester has the formula:

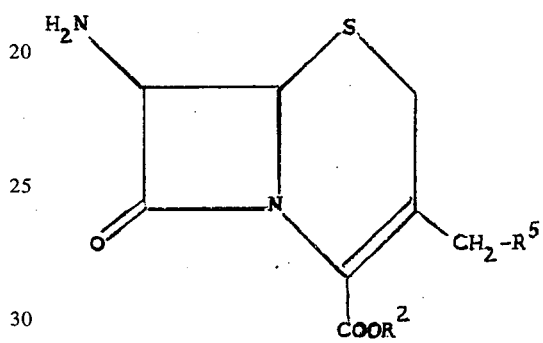

and acid addition salts thereof, wherein $R^2$ is a carboxylic acid protecting group and wherein $R^5$ is hydrogen, acetoxy or a heterocyclic thio group.

3. Process according to claim 1, wherein the α-aminoacetic acid has the general formula:

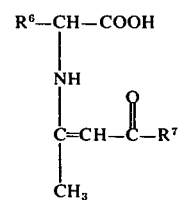

where $R^7$ is $C_{1-4}$ alkyl or $C_{1-4}$ alkoxy, and $R^6$ is a thienyl group, or a phenyl or cyclohexa-1,4-dienyl group optionally substituted by $C_{1-4}$ alkyl, $C_{1-4}$ alkoxy, halogen, hydroxy, amino, substituted amino, nitro or trifluoromethyl.

4. Process according to claim 3, wherein $R^6$ is unsubstituted phenyl, cyclohex-1,4-dienyl or thienyl and $R^7$ is methoxy.

5. Process according to claim 1 for preparing cephalexin wherein the 4-carboxylic acid ester is the p-nitrobenzyl ester of 7-aminodesacetoxycephalosporanic acid and wherein the activated form of the α-aminoacetic acid is N-(2-methoxycarbonyl-1-methylvinyl)-D-α-phenylglycine.

* * * * *